United States Patent [19]
Laube

[11] Patent Number: 5,149,435
[45] Date of Patent: Sep. 22, 1992

[54] MOLECULAR SIEVE ARRANGEMENT AND FILTERING METHOD FOR REMOVAL OF A SELECTED CONSTITUENT

[75] Inventor: Hans-Jürgen Laube, Siegershausen, Switzerland

[73] Assignee: H J L Projects & Developments Ltd., Düdingen, Switzerland

[21] Appl. No.: 415,252

[22] PCT Filed: Jan. 6, 1989

[86] PCT No.: PCT/CH89/00002

§ 371 Date: Sep. 6, 1989

§ 102(e) Date: Sep. 6, 1989

[87] PCT Pub. No.: WO89/06156

PCT Pub. Date: Jul. 13, 1989

[30] Foreign Application Priority Data

Jan. 7, 1988 [CH] Switzerland .............................. 26/88

[51] Int. Cl.$^5$ ...................... B01D 61/00; B01D 39/00
[52] U.S. Cl. ........................... 210/651; 55/75;
55/389; 55/524; 210/263; 210/266; 210/502.1;
210/504; 210/506; 210/507; 210/509; 210/679;
502/60; 502/62; 502/64; 502/69; 502/87
[58] Field of Search ............ 210/263, 266, 269, 502.1,
210/503, 504, 505, 506, 651, 679, 222, 695, 507,
508, 509; 55/75, 389, 524; 502/60, 64, 69, 77,
87, 62

[56] References Cited

U.S. PATENT DOCUMENTS

| | | | |
|---|---|---|---|
| 4,056,471 | 11/1977 | Fischer et al. | 210/269 |
| 4,081,402 | 3/1978 | Levy et al. | 424/78 |
| 4,220,632 | 9/1980 | Pence et al. | 423/239 |
| 4,273,621 | 6/1981 | Fornoff | 55/75 |
| 4,567,152 | 1/1986 | Pine | 502/69 |
| 4,606,824 | 8/1986 | Chu | 210/635 |
| 4,645,519 | 2/1987 | Fraioli et al. | 55/389 |
| 4,650,621 | 3/1987 | Sago et al. | 427/344 |
| 4,732,887 | 3/1988 | Obanawa et al. | 210/679 |
| 4,809,247 | 1/1982 | Hou | 162/149 |
| 4,919,907 | 4/1990 | Occelli | 502/61 |
| 5,071,450 | 12/1991 | Cabrera et al. | 55/75 |
| 5,091,080 | 2/1992 | van Eikeren et al. | 210/502.1 |

FOREIGN PATENT DOCUMENTS 2005019 4/1979 United Kingdom .

Primary Examiner—Robert A. Dawson
Assistant Examiner—Sun Uk Kim
Attorney, Agent, or Firm—Peter K. Kontler

[57] ABSTRACT

A molecular sieve material is combined with a porous carrier material. The pores of the molecular sieve material are impermeable to molecules or organisms having a size equal to or greater than that of the water molecule either because the molecular sieve material is selected so as to have pores which are smaller than such molecule or because the pores of the molecular sieve material are closed by a film. The pores of the molecular sieve material thus remain unoccupied and are able to exert an attractive force on molecules or organisms which are to be captured. The pores of the carrier material are designed to accept molecules or organisms having a size equal to or greater than that of the water molecule so that, when such molecules or organisms are attracted by the molecular sieve material, they can be trapped in the carrier material.

23 Claims, 1 Drawing Sheet

MOLECULAR SIEVE ARRANGEMENT AND FILTERING METHOD FOR REMOVAL OF A SELECTED CONSTITUENT

BACKGROUND OF THE INVENTION

The present invention relates to a molecular sieve arrangement.

Natural and synthetic zeolitic molecular sieves are suitable for the separation of mixtures of inorganic and organic substances and for the removal of undesired impurities from gases and liquids. One current field of application of molecular sieves is the drying of gases and liquids, for example, acetone, butane, toluene, etc.

Molecular sieves are also used for the removal of carbon monoxide, hydrocarbons, nitrogen, methane and so on from air. They are further used in ion exchangers.

Molecular sieves within the scope of the invention can consist of natural or synthetic zeolites. Synthetic zeolites frequently have the same crystal structure as natural zeolites. Natural zeolites may, for example, be aluminum silicates having the general formula $$\text{Me}_{\frac{2}{n}}\text{O}\cdot\text{Al}_2\text{O}_3\cdot n\text{SiO}_2\cdot p\text{H}_2\text{O}$$

where Me denotes the alkali metal ion (n=1), mostly Na or K, or the alkaline earth metal (n=2) which is normally Ca and more seldom Ba, Sr and Mg. Most of the ad/absorbents are included in this category.

The mechanics of separating molecules from liquid or gaseous media by means of molecular sieves involves adsorption with the molecular sieve functioning as an adsorbent and influencing the adsorption through the magnitude and energy characteristics of its surface. The adsorption of ions, molecules or molecular agglomerates and the like—the adsorbates—is limited by the energy characteristics of the boundary layer between the two phases. The adsorbed molecules continuously coat the inner surface of the adsorbent and cover the same. Accordingly, saturation occurs after a certain amount of time and prevents further adsorption.

The known separating processes use only molecular sieves having a pore size of 3 Angstroms or greater than 3 Angstroms in order to permit the entry of molecules to be filtered out of gases or liquids, that is, in order to make the vast inner surface of the molecular sieve usable.

The zeolites of the natural analcite group, whose pores have a size of the order of 2.6 Angstroms, have not been used as molecular sieves because the molecules to be adsorbed or absorbed cannot, due to their size, penetrate into the primary pores of the analcite zeolite. The smallest molecule, which is the water molecule, measures only about 2.9 Angstroms (see "MOLEKULARSIEBE" by Otto Grubner, Pavel Jiru and Milos Ralek, VEB Deutscher Verlag der Wissenschaften, Berlin 1968, page 27).

The disadvantageous property of the known molecular sieves is that the inner surfaces thereof are directly loaded and, depending upon molecular sieve type, no further molecules can be taken up once the adsorbate proportion has increased to about 25%.

Loading of the inner surfaces of the conventional molecular sieves already occurs upon contact with the surrounding air and the water molecules contained therein. Accordingly, the capacity is reduced in two respects.

SUMMARY OF THE INVENTION

The invention here provides a remedy.

The invention, solves the problem of creating a molecular sieves arrangement which can filter molecules or microscopic particles from gases or liquids and in which the inner surfaces of the molecular sieve can be coated neither by water molecules nor by the filtered molecules.

A molecular sieve which is incorporated in a carrier material and has a pore size smaller than 3 Angstroms (primary pores) allows the molecules or particles to be filtered to be brought into the pore and channel structure of the carrier material; the inner surfaces of the molecular sieve having pores smaller than 3 Angstroms remain largely free and retain their static charge (Coulombic attraction).

The pore and channel structure of the carrier material can have cross sections which are larger than the pores of the molecular sieve by a factor of up to 1000 and more. Correspondingly larger quantities of particles to be filtered can be accumulated in these relatively vast inner cavities before the static attraction of the adsorbent is no longer sufficient to draw additional charged particles into the channel structure of the carrier material. Water present in the carrier material, which can serve as a transporting medium, is successively pushed out of the channels by charged particles to be accumulated. The capacity thus depends, for one, on the attractive forces of the zeolitic material; the particle size of the accumulated charged particles has no significant influence on the quantitative capacity.

Hence, this mechanism favors highly polar particles, e.g., viruses; molecules having lower values can again be pushed out of the channel structure and through the surface pores of the carrier material. A selection, which is controlled by appropriate choice of the channel cross sections and surface pores of the carrier material, that is, by the secondary pore structure and channel structure, accordingly also becomes possible. Due to the possibility of placing zeolites having pores smaller than 3 Angstroms and constituting part of the molecular sieve arrangement according to the invention directly in aqueous media, viruses or stimulating agents in general can be filtered out of liquids, e.g., blood or blood plasma.

For use in blood, the composite material of adsorbent and porous carrier material is preferably preloaded with water so that no water but only particles capable of being caught by polar effects can be removed from the medium to be filtered. For use in gaseous media, the carrier material cavities can be preloaded with an inert gas.

A further advantage of the composite material of the invention is the energy saving during desorption of the adsorbate. Since the accumulated particles are stored only in the channel structure of the carrier material and are not adsorbed on the inner surfaces of the zeolitic material, a regeneration or rinsing out can be accomplished with substantially less energy and, consequently, also at lower temperatures. The choice of the carrier material is thereby simplified, that is, synthetic resins, e.g., in the form of fibers as carrier materials, having a large surface area and, accordingly, superior dynamics, can also find application as reusable composite materials.

Adsorbents which are smaller than 3 Angstroms and are incorporated in non-combustible, porous carrier materials, e.g., stone, pumice, clays, porous metals, etc., can be used for the purification of exhaust gases from combustion machines. Here, regeneration by washing is possible.

In another advantageous embodiment of the invention, similar results can be achieved using conventional zeolites whose pores are larger than 3 Angstroms and are agglutinated, for example, if zeolite pores larger than 3 Angstroms are covered and closed by a film or skin which is impermeable to water molecules to thereby prevent the entry of water molecules. The skin can consist of metal, e.g., aluminum. The inherent attractive force of the zeolites or molecular sieves can thus not be nullified by water molecules accumulated in the channel structure of the carrier material. The ad/absorption forces of the molecular sieve particles having pores larger than 3 Angstroms remains in existence as in the zeolites with pores smaller than 3 Angstroms.

In comparison to activated carbon, the composite material according to the invention accordingly exhibits substantially greater dynamics and capacity, lower energy consumption during desorption (regeneration) and, in addition, better stability as regards shape. In the form of capsules or tablets, the composite material can be ingested instead of activated carbon, e.g., to take up particles such as viruses, bacteria and the like present in stomach/intestinal juices. By including hard magnetic additions in the composite, the composite and the trapped particles can be readily separated after travelling through a conveying section in the medium to be purified.

The greatest dynamics of the product according to the invention are achieved in the form of fibers since these have a very large surface area per unit weight and yet, in the form of a fleece, for example, can be readily handled in liquid and gaseous media.

In the form of fiber clippings to which another component has been added, the material of the invention can be brought into circulation, e.g., in the blood vessels of a living being, and subsequently again removed from circulation by suitable means, e.g., magnetic fields if the other component is magnetically engageable. Since the other component preferably does not have an attractive force itself, agglomerates in the circulatory path can be avoided.

By incorporating the composite material of the invention in liquids, salves or cremes which are preferably hygroscopic, access of stimulating agents to wounds can be prevented and, at the same time, stimulating agents present at the wound can be removed therefrom.

BRIEF DESCRIPTION OF THE DRAWINGS

The invention is more fully described with reference to specific embodiments illustrated in the accompanying drawings wherein.

DESCRIPTION OF THE PREFERRED EMBODIMENTS

Figure 1:
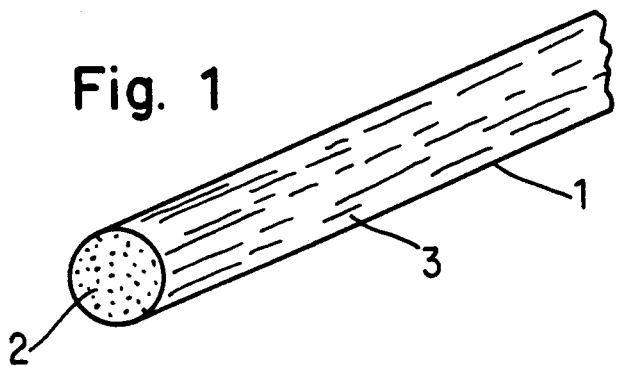
FIG. 1 shows a greatly enlarged fiber having zeolites incorporated therein.

FIG. 1 illustrates a section of a fiber 1 in which zeolites 2 are incorporated in the form of an ultrafine powder or granulate. The incorporation of the zeolites 2 in the carrier structure, that is, in the material of which the fiber 1 is made, is not the subject of this invention. There are various possibilities for adding the zeolite component 2 during the spinning process for the fiber 1.

The fiber 1 itself consists of a material with an open pore structure. This allows the take-up and release of water and water vapor. Fibers 1 without zeolites 2 and capable of taking up water vapor are known; a method for the production of such a fiber 1 is described, for example, in European patent application 0 029 949 and in the publication Chemiefasern/Textilindustrie, 31/82, pages 112–116 (1981).

When zeolite particles 2 with primary pores larger than 3 Angstroms are incorporated in such a fiber 1 whose pores 3 and channels 4 have a cross section of approximately 1000 nm, then this can be used to filter from the environment particles such as viruses, bacteria and molecules which can penetrate into the carrier material through the pores (secondary pores) 3 on the surface thereof and are drawn by the attractive forces of the zeolites 2. Since the water molecules of approximately 2.9 Angstrom size are always smaller than the (primary) pores of an incorporated conventional zeolite of 3 Angstrom size or greater than 3 Angstrom size and arrive at the inner surfaces of the zeolites 2 via the primary pores, the effectiveness of the zeolites 2 in the free atmosphere or in a liquid medium is low because of rapid loading with water molecules.

Due to the accumulation, i.e., adsorption, of molecules through its primary pores 13, the attractive force of a grain of conventional molecular sieve granulate decreases steadily and rapidly in the free atmosphere until a maximum loading, namely, approximately 25 percent by weight, is achieved.

Figure 4:
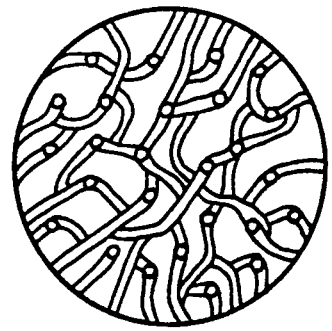
FIG. 4 is a section through a fiber having zeolite particles with a pore size smaller than 3 Angstroms (unloaded)
Figure 5:
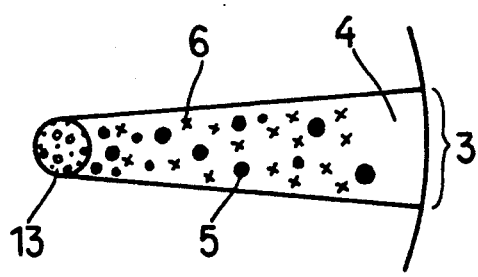
FIG. 5 is an enlarged illustration of a pore or channel in a fiber according to FIG. 4.

If now, in accordance with the invention and as illustrated in FIGS. 4 and 5, zeolites 2 having a pore size smaller than 3 Angstroms, e.g., 2.6 Angstroms, are incorporated in the fiber 1, then the molecules and particles 5, etc., entering through the channels 4 of a porous fiber 1 can penetrate only to the vicinity of the incorporated zeolite particles; entry into the primary pores 13, in contrast, is not possible. Even the water molecule 6 is unable to load the primary pores (diameter of 2.6 Angstroms, for example) of zeolites of the analcite group (see FIG. 5). In this manner, the attractive force of the zeolites 2 is mostly retained and the secondary pore structure of the carrier material, which is preferably selected so as to have sizes in the nanometer/micron range, takes up and holds a very large quantity of particles and molecules, as well as bacteria, viruses and the like, capable of being caught by polar effects. The attractive force of the zeolite crystals remains high even with loaded carrier material channels so that particles having high polarity values can diffuse through the channel structure which is, for example, loaded with water. The corresponding proportion of water is pushed outwards. Further loading is terminated only when an equilibrium is reached between adsorbent and adsorbate. If the zeolitic material is bound in plastics, then the alkaline zeolitic material (pH value approximately 11.5) can also be used in substances susceptible to alkalis since direct contact with the medium to be purified, e.g., in the nutrient and hygienic fields, is now prevented. Suitable carrier materials for this purpose are polyamides and polyacrylics, for example, as well as activated carbon; also soil and metals for applications requiring resistance to heat.

The mechanism according to the invention can also be closely achieved with conventional zeolites 2 having pores larger than 3 Angstroms in that the pores 13 are covered or closed by a film or skin so as to be sealed against water molecules. The inherent attractive force of the zeolites or microsieves can then no longer be annulled by accumulated water molecules in the channel structure of the carrier material. As in the zeolites having pores smaller than 3 Angstroms, the ad/absorption forces remain operative.

As already indicated above, it now becomes possible, by way of example, to separate bacteria having a size of 2 microns, for instance, or viruses having a size between about 8 and 400 nm, for example, from liquids or the gas phase. The viruses, in particular, have a highly charged surface and are thus drawn into the (secondary) channel structure of the carrier material by the charge of the adsorbents bound in the carrier material. Since water molecules cannot enter the primary pores of the zeolite, the viruses are held back in the channel structure of the carrier material. The water molecules are subsequently again successively pushed out of the channel structure of the carrier material via the surface pores thereof by the particles drawn to the zeolite. The water accordingly functions as a transporting medium. It becomes possible to draw and accumulate the most diverse particles, bacteria and viruses, as well as pesticides, from the environment by means of a carrier material which has been preloaded with water.

It is possible, for example, to manufacture a mouth and nose protector having a fleece which is made of fibers and the molecular sieve arrangement of the invention and which constitutes a filter against the penetration of viruses, bacteria and so on to thereby prevent infections via the respiratory tract (influenza, colds, adeno-infections, corona infections and viral infections) as well as other infections (smallpox, rubella, chickenpox, mumps, measles, etc.). By means of the mentioned filter, viruses bound to the drops which are generated upon sneezing are caught and held back.

The textile fiber, cotton wool or fleece according to the invention can be used as a cotton wool plug, as a protective breathing mask or as a filter in ventilating and air conditioning systems.

Since, due to incorporation in a porous carrier material, the alkaline properties of the zeolitic material no longer affect the substances to be purified, it is possible to purify blood and plasma from particles such as bacteria, viruses, etc. in that the blood and plasma are passed through a tube filled with appropriately prepared fiber material and, after passage, are again conveyed to the human or animal body.

If hard magnetic metallic material, e.g., ($MeCO_3 + FeO_3$), is additionally mixed with the composite, then the composite particles, e.g., in the form of fiber clippings, circulating in the liquid to be purified can be localized and once again separated. These fiber clippings accordingly have the action of a killer cell which catches particles (viruses, bacteria, etc.) swimming along therewith in the liquid. Such a killer cell can, for instance, consist of fiber clippings produced from porous material and having the molecular sieve arrangement in accordance with the invention. The pores (primary pores) of the synthetic zeolite crystal have a diameter of less than 3 Angstroms, e.g., 2.6 Angstroms. The synthetic fiber exhibits a pore structure having a diameter of 1000 nanometers, for example. The fiber clipping itself has a diameter of about 8 microns and a length of 8 to 10 microns which is a size approximating that of a T4 helper lymphocyte. As already indicated above, $MeCO_3$ and $FeO_3$ can, for instance, be added as hard magnetic material and can take the form of oxidized or sintered material which has been ground to a particle size of about 0.2 micron.

These fiber clippings can be placed in a liquid, e.g., the circulatory system or preserved blood plasma, and again separated after a certain amount of time by means of magnetic fields.

A fibrous fleece material of the same composition as the fiber clippings which contain the hard magnetic particles (and are thus capable of being caught) can be used for separation. The fibrous fleece material is, however, additionally magnetized and holds back the magnetically engageable fiber clippings flowing through the same.

Use is possible not only in organic liquids but also for the filtration of liquid nutrients. If necessary, the fibers/fiber clippings are here preloaded with water under sterile conditions prior to use.

Figure 2:
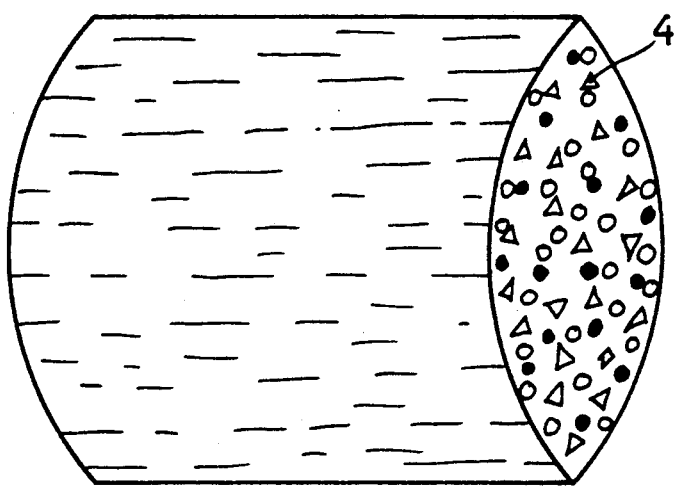
FIG. 2 shows a synthetic killer cell (in the form of a fiber clipping) enlarged about ten thousand times.
Figure 3:
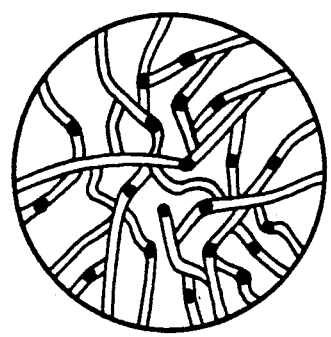
FIG. 3 is a section through a fiber having zeolite particles with a pore size greater than 3 Angstroms (loaded)

The just described synthetic killer cells can be used for the isolation of known and unknown stimulants/virus types if these are extracted from the composite material by vacuum techniques, for example, after passage through the circulatory system. It is self-understood that synthetic killer cells can also be locally inserted in the lymphatic system. For a better understanding of the size relationships, FIG. 2 shows a synthetic killer cell at an enlargement of about ten thousand times.

Aside from the described applications in the trapping of viruses, bacteria and the like, the composite material can be used in an appropriate form, e.g., with a heat-resistant material such as clay, etc., for the purification of exhaust gases from combustion engines, e.g., at the outlet of the muffler or as a separate interchangeable part.

Filters made of the composite material according to the invention can also be used in air conditioning and ventilating systems of buildings and vehicles, as well as in household vacuum cleaners, and make it possible to filter out not only dust particles but also stimulants (viruses, bacteria, etc.) detrimental to health since the zeolitic material component with primary pores of approximately 2.6 Angstroms is not directly loaded, and its action is not cancelled, by the omnipresent water molecules.

An application is also possible as a lining in shoes to prevent the accumulation of spores which can result in a foot fungus.

There further exists the possibility of using the composite material for the drying of air in the air brakes of vehicles whereby, as compared to the conventional zeolitic granulate with a primary pore size of 3 Angstroms and up, it is possible to achieve an approximately fourfold increase in moisture capacity or to operate with a substantially smaller volume.

Another area of application is in insulating glass spacers, e.g., where fibers made of the composite material are in the form of a plait.

Inserts produced from the composite material and provided in the closures of containers or on the inner surfaces thereof function to protect the contents against moisture or to dehydrate the contents.

A further application of fibers made from the composite material of the invention is in the production of filter mats, operating cloths, handkerchiefs, baby napkins and other hygienic articles. The fibers worked into the handkerchief material (cellulose) remove particles such as viruses, etc. which adhere to the moisture applied to the material. The usual spreading of infection via the handkerchief upon reuse is thus very greatly reduced. Analogously, other cloths, as well as tampons, in the hygienic field can be enriched with the fiber of the invention.

In large industrial installations, the composite material can be used to filter out pesticides and the like contained in water. As already mentioned earlier, a regeneration of the filter composite material can be achieved with little energy consumption.

Another possibility for use of the composite material is in the binding of viruses on plants. If the composite material in the form of fiber clippings is mixed with fruit wax, for example, and applied to plants by spraying, then the plants are protected against stimulants, e.g., tobacco mosaic bacilli and viruses from tobacco plants.

I claim:

1. A filter substance for the removal of a selected constituent from a fluid containing a plurality of constituents, said substance comprising a carrier material having first pores; and a molecular sieve material having second pores, said second pores being smaller than said first pores and too small to permit entry of the selected constituent thereinto and being bounded by internal surfaces which generate an attractive force for attracting the selected constituent to, and holding the selected constituent in said first pores, and said molecular sieve material being selected or designed to substantially prevent accumulation of any constituent of the fluid on said internal surfaces.

2. The substance of claim 1, wherein said materials are bound to one another.

3. The substance of claim 1, wherein said second pores have a size smaller than 3 Angstroms and said first pores have a size larger than 3 Angstroms.

4. The substance of claim 3, wherein said molecular sieve material comprises a zeolite of the analcite group.

5. The substance of claim 3, wherein said second pores have a size of approximately 2.6 Angstroms.

6. The substance of claim 1, wherein said materials constitute part of a composite and are bound to one another, said composite being fibrous.

7. The substance of claim 1, wherein said materials constitute part of a composite and said composite is in the form of at least one ingestible tablet.

8. The substance of claim 1, wherein said carrier material is heat-resistant.

9. The substance of claim 1, wherein said first pores are channel-like.

10. A filtering method, comprising the steps of contacting a fluid with a filter substance containing a porous carrier material and a porous molecular sieve material having internal surfaces which generate an attractive force; drawing a selected constituent of said fluid into said carrier material using said attractive force; and substantially preventing accumulation of any constituent of said fluid on said internal surfaces.

11. The method of claim 10, wherein said selected constituent comprises a multiplicity of molecules.

12. The method of claim 10, wherein said selected constituent comprises a multiplicity of microscopic particles.

13. The method of claim 10, wherein said fluid comprises blood or blood plasma and said selected constituent includes bacteria or a virus.

14. The method of claim 10, wherein said fluid comprises stomach juices and said selected constituent includes microscopic particles, bacteria or a virus.

15. An article of manufacture, comprising a base member; and a filter substance for the removal of a selected constituent from a fluid containing a plurality of constituents, said substance applied to said base member and including a carrier material having first pores, and a molecular sieve material having second pores, said second pores being bounded by internal surfaces which generate an attractive force for attracting the selected constituent to, and holding the selected constituent in said first pores, and said molecular sieve material being selected or designed to substantially prevent accumulation of any constituent of the fluid on said internal surfaces.

16. The article of claim 15, wherein said base member comprises a textile.

17. The article of claim 15, wherein said base member is selected from the group consisting of mats, handkerchiefs, baby napkins, bandages and operating cloths.

18. The article of claim 15, wherein said base member comprises an ingestible capsule.

19. A composition of matter, comprising a base substance; and a filter substance for the removal of a selected constituent from a fluid containing a plurality of constituents, said filter substance including a carrier material having first pores, and a molecular sieve material having second pores, said second pores being bounded by internal surfaces which generate an attractive force for attracting the selected constituent to, and holding the selected constituent in said first pores, and said molecular sieve material being selected or designed to substantially prevent accumulation of any constituent of the fluid on said internal surfaces.

20. The composition of claim 19, wherein said base substance comprises a liquid, paste or cream and said filter substance is incorporated in said base substance to form a hygroscopic composite.

21. Molecular sieve arrangement for the filtration of molecules or microscopic particles from gases and liquids, comprising a granulated or particulate molecular sieve material which has channels and primary pores and is bound in a porous carrier material, the primary pores of the molecular sieve material being constituted in such a manner that adsorption and absorption of water and gas molecules are prevented and no direct loading occurs at the inner surfaces of the molecular sieve material, the molecular sieve material having a pore size greater than 3 Angstroms, and the pores and channels of the molecular sieve particles or granulate being closed at the surface by a film or skin which is impermeable to water molecules.

22. The molecular sieve arrangement of claim 21, wherein the film or skin consists of metal.

23. A filter substance for the removal of a selected constituent from a fluid containing a plurality of constituents, said substance comprising a carrier material having first pores with a size larger than 3 Angstroms; and a molecular sieve material having second pores with a size smaller than 3 Angstroms, said second pores being bounded by internal surfaces which generate an attractive force for attracting the selected constituent to, and holding the selected constituent in said first pores, and said molecular sieve material being selected and designed to substantially prevent accumulation of any constituent of fluid on said internal surfaces.

* * * * *